(12) United States Patent
Lee et al.

(10) Patent No.: US 11,186,616 B2
(45) Date of Patent: Nov. 30, 2021

(54) INCREASED PRODUCTION OF GINSENOSIDES THROUGH YEAST CELL ORGANELLE IMPROVEMENT

(71) Applicant: KOREA RESEARCH INSTITUTE OF CHEMICAL TECHNOLOGY, Daejeon (KR)

(72) Inventors: Ju Young Lee, Gyeonggi-do (KR); In Seung Jang, Busan (KR); Seohyun Kim, Busan (KR); Sun-Chang Kim, Daejeon (KR); Suk Chea Jung, Daejeon (KR); Jong Geon Jegal, Ulsan (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 0 days.

(21) Appl. No.: 17/026,814

(22) Filed: Sep. 21, 2020

(65) Prior Publication Data

US 2021/0002334 A1 Jan. 7, 2021

Related U.S. Application Data

(62) Division of application No. 15/880,838, filed on Jan. 26, 2018, now abandoned.

(30) Foreign Application Priority Data

May 2, 2017 (KR) .......................... 10-2017-0056258

(51) Int. Cl.
| | | |
|---|---|---|
| C12P 19/28 | (2006.01) | |
| C12P 19/56 | (2006.01) | |
| C12N 15/81 | (2006.01) | |
| C07K 14/395 | (2006.01) | |
| C12P 33/20 | (2006.01) | |
| C12N 9/02 | (2006.01) | |

(52) U.S. Cl.
CPC ............ *C07K 14/395* (2013.01); *C12N 15/81* (2013.01); *C12P 19/56* (2013.01); *C12P 33/20* (2013.01); *C12N 2501/60* (2013.01)

(58) Field of Classification Search
CPC ..... C12N 15/81; C12N 2501/60; C12P 33/20; C12P 19/56; C07K 14/395
USPC ............................ 435/53, 75; 424/439, 70.13
See application file for complete search history.

(56) References Cited

FOREIGN PATENT DOCUMENTS

| CN | 105 255 952 A | 1/2016 |
|---|---|---|
| JP | 06-209762 | 8/1994 |
| WO | WO 2008-000277 | 1/2008 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Chumnanpuen et al., "Integrated analysis, transcriptome-lipidome, reveals the effects of INO-level (INO2 and INO4) on lipid metabolism in yeast," *BMC Systems Biology*, 7(Suppl. 3):S7, 2013.
Dai et al: "Producing aglycons of ginsenosides in bakers' yeast", Scientific Reports, vol. 4, No. 1, Jan. 15, 2014 (Jan. 15, 2014), XP55471751.
Dai, Zhubo, et al. "Metabolic engineering of *Saccharomyces cerevisiae* for production of ginsenosides." *Metabolic engineering* 20 (2013): 146-156.
De Ruijter et al: "Enhancing antibody folding and secretion by tailoring the *Saccharomyces cerevisiae* endoplasmic reticulum", Microbial Cell Factories, vol. 15, No. 1, May 23, 2016 (May 23, 2016), XP055473458.
Devos, Damien, and Alfonso Valencia. "Practical limits of function prediction." *Proteins: Structure, Function, and Bioinformatics* 41.1 (2000): 98-107.
Extended European Search Report issued in European Patent Application No. 18154635.9, dated May 18, 2018.
GenBank: CP004708.2, "*Saccharomyces cerevisiae* YJM1307 chromosome IV sequence", dated Dec. 15, 2016.
GenBank: 05267.1, "*Saccharomvces cerevisiae* transcription regulator (INO4) gene, complete eds", dated Oct. 26, 2009.
Kisselev, Lev. "Polypeptide release factors in prokaryotes and eukaryotes: same function, different structure." *Structure* 10.1 (2002): 8-9.
Lee, Ju Young, et al. "Engineering cellular redox balance in *Saccharomyces cerevisiae* for improved production of L-lactic acid." *Biotechnology and bioengineering* 112.4 (2015): 751-758.
NCBI Reference Sequence: NM_001179100.1, "*Saccharomyces cerevisiae* S288c transcriptional regulator OPI1 (OPI1), partial mRNA", dated Mar. 15, 2017.
Peng, Bingyin, et al. "Controlling heterologous gene expression in yeast cell factories on different carbon substrates and across the diauxic shift: a comparison of veast promoter activities." *Microbial cell factories* 14.1 (2015): 1-11.
Schuck, Sebastian, et al. "Membrane expansion alleviates endoplasmic reticulum stress independently of the unfolded protein response." *The Journal of cell biology* 187.4 (2009): 525-536.
Schwank, et al., "Influence of gene dosage and autoregulation of the regulatory genes INO2 and INO4 on inositol/choline-repressible gene transcription in the yeast *Saccharomyces cerevisiae*." *Current genetics* 31.6 (1997): 462-468.

(Continued)

Primary Examiner — Tekchand Saidha
Assistant Examiner — Mohammad Y Meah
(74) Attorney, Agent, or Firm — Parker Highlander PLLC

(57) ABSTRACT

Provided are a recombinant yeast having improved ability to produce ginsenoside, which is prepared by overexpressing INO2 and INO4 or deleting OPT1 in a yeast having ability to produce ginsenoside, a method of preparing the yeast, and a method of producing ginsenoside by using the yeast.

2 Claims, 3 Drawing Sheets

Specification includes a Sequence Listing.

(56) References Cited

OTHER PUBLICATIONS

Spanova, Miroslava, et al. "Influence of squalene on lipid particle/droplet and membrane organization in the yeast *Saccharomyces cerevisiae*." *Biochimica et Biophysica Acta (BBA)—Molecular and Cell Biology of Lipids* 1821.4 (2012): 647-653.
Teo W S et al: "Metabolic engineering of *Saccharomyces cerevisiae* for production of fatty acid short- and branched-chain alkyl esters biodiesel", Biotechnology for Biofuels, Biomed Central Ltd, GB, vol. 8, Nov. 1, 2015 (Nov. 1, 2015), pp. 177-185, XP002754828.
Whisstock, James C., and Arthur M. Lesk. "Prediction of protein function from protein sequence and structure." *Quarterly reviews of biophysics* 36.3 (2003): 307.
Witkowski, Andrzej, et al. "Conversion of a β-ketoacyl synthase to a malonyl decarboxylase by replacement of the active-site cysteine with glutamine." *Biochemistry* 38.36 (1999): 11643-11650.
Ohto Chikara et al., "Overexpression of the gene encoding HMG-CoA reductase infor production of prenyl alcohols", *Applied Microbiology and Biotechnology*, 82:5, pp. 837-845, XP037016524, 2009.
Office Communication issued in European Application No. 18154635.9, dated Mar. 2, 2021.

\* cited by examiner

[FIG. 1]
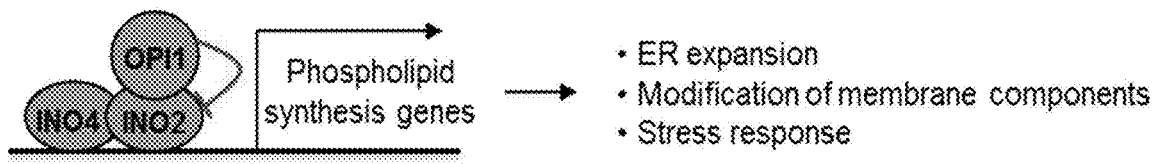
[FIG. 2]
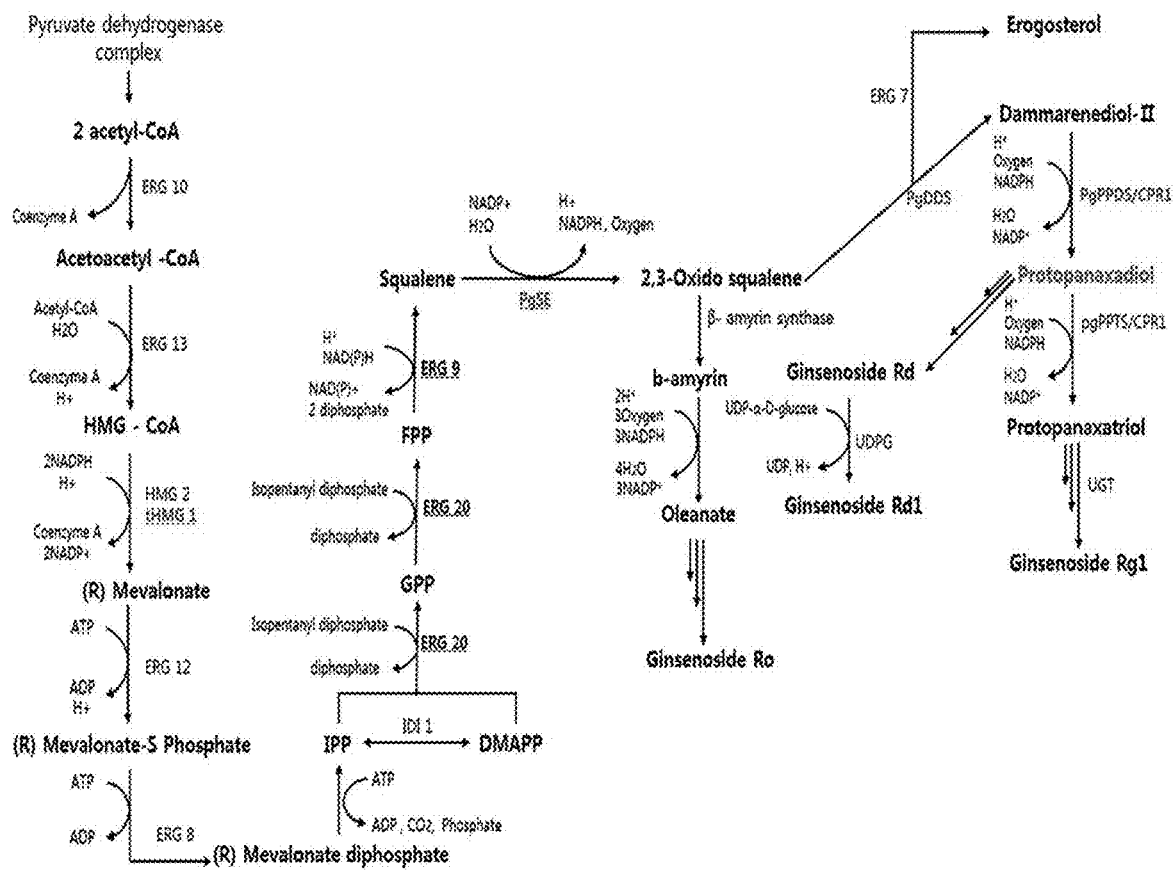

[FIG. 3]
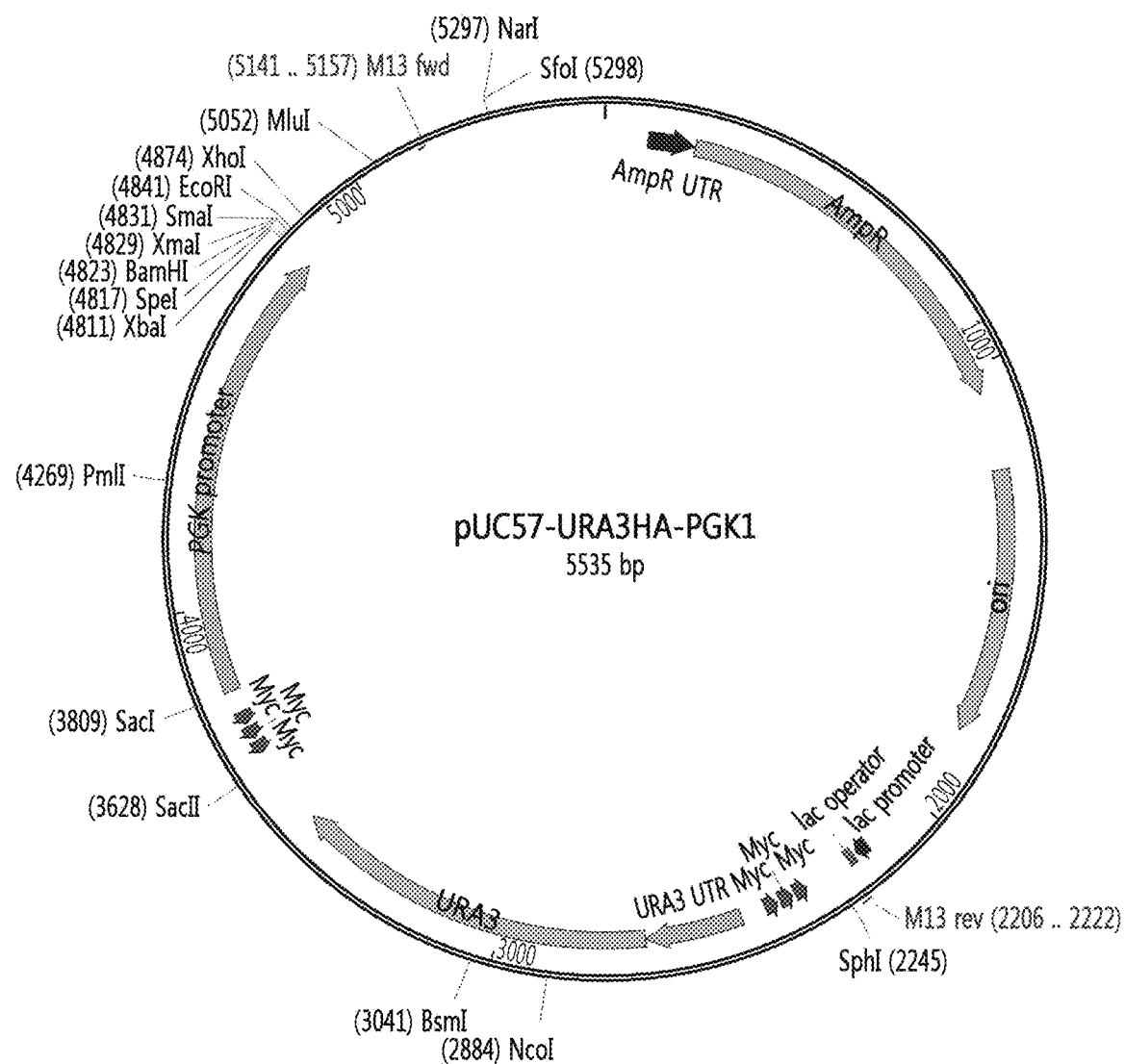

[FIG. 4]
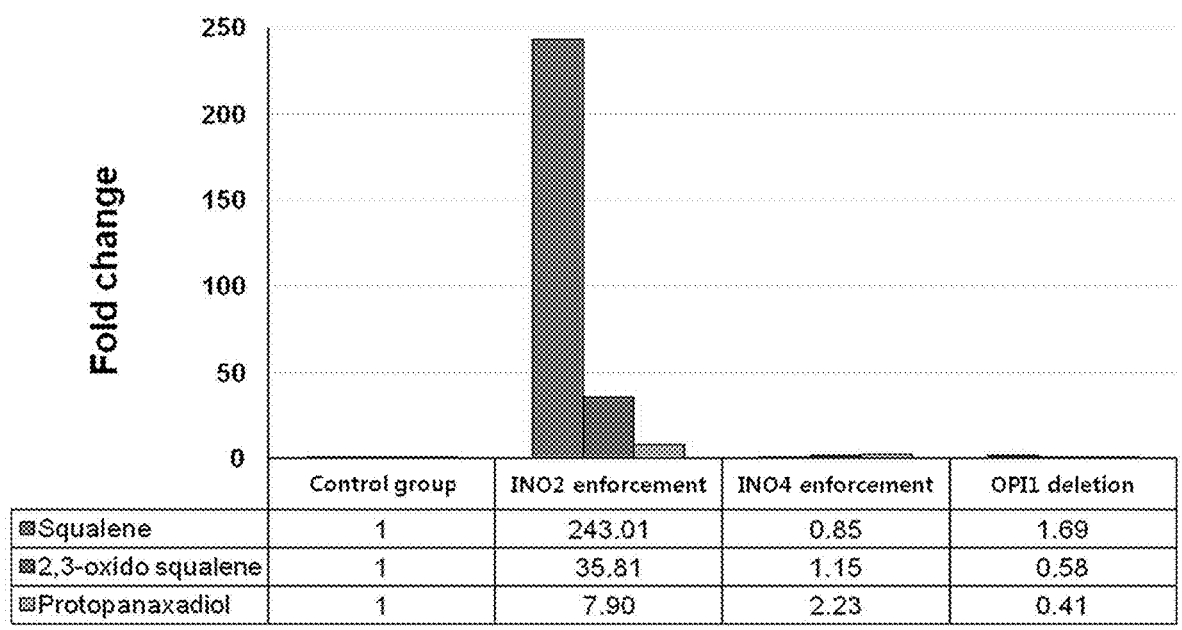

SEQUENCE LISTING

<160> NUMBER OF SEQ ID NOS: 22

<210> SEQ ID NO 1
<211> LENGTH: 915
<212> TYPE: DNA
<213> ORGANISM: Saccharomyces cerevisiae

<400> SEQUENCE: 1

| | | |
|---|---|---|
| atgcaacaag caactgggaa cgaattactg ggtatcctag atctggataa cgatatagac | 60 |
| tttgaaactg cttaccaaat gctcagcagt aacttcgacg accaaatgtc tgcgcacata | 120 |
| catgaaaaca cgtttagtgc aacttcccct cctctgttaa cacacgagct cggcataatt | 180 |
| cctaacgtgg caaccgtgca accctctcac gtagaaacta tacctgccga taaccaaact | 240 |
| catcatgctc ctttgcatac tcatgctcac tatctaaatc acaaccctca tcaaccaagc | 300 |
| atgggttttg atcaaacgct tggtctcaag ttgtctcctt ccagttcggg gttgttgagc | 360 |
| acgaatgaat cgaatgccat tgaacagttt ttagacaatc taatatcaca ggatatgatg | 420 |
| tcttccaacg cttccatgaa ctccgattca catctacata aagatcacc aaaaaagcag | 480 |
| cataggtata ccgaattaaa tcaaagatat cctgaaacac atccacacag taacacaggg | 540 |
| gagttaccca caaacacagc agatgtgcca actgagttca ccacgaggga aggacctcat | 600 |
| cagcctatcg gcaatgacca ctacaacccg ccaccgtttt cagtacctga gatacgaatc | 660 |
| ccagactctg atattccagc caatatcgag gacgaccctg tgaaggtacg gaaatggaaa | 720 |
| cacgttcaaa tggagaagat acgaagaata aacaccaaag aagcctttga aaggctcatt | 780 |
| aaatcagtaa ggaccccacc aaaggaaaac gggaaaagaa ttcccaagca tattctttta | 840 |
| acttgtgtaa tgaacgatat caagtccatt agaagcgcaa atgaagcact acagcacata | 900 |
| ctggatgatt cctga | 915 |

<210> SEQ ID NO 2
<211> LENGTH: 456
<212> TYPE: DNA
<213> ORGANISM: Saccharomyces cerevisiae

<400> SEQUENCE: 2

| | | |
|---|---|---|
| atgacgaacg atattaagga gatacaaaca atacagccgg gattgtccga gattaaggag | 60 |
| ataaagggtg aactggctaa tgtgaagaaa aggaaacgca ggtctaagaa gattaataaa | 120 |
| ttgactgatg gtcaaatacg tataaatcat gtttcgtctg aaaaaaaaag gagagaattg | 180 |
| gaaagagcta tatttgacga actggtagca gtagtacctg acctgcaacc ccaggaaagt | 240 |
| cggtcagaac taatcatata cctgaaaagc ttgagttact taagttggtt gtatgaaagg | 300 |
| aatgaaaagc tgagaaaaca atcatagct aagcatgagg caaaaccgg cagcagcagc | 360 |
| agcagcgatc ccgtacaaga acaaaatgga acattcggg atttagtacc gaaggagtta | 420 |
| atttgggagc tgggtgatgg acagagtggt cagtga | 456 |

<210> SEQ ID NO 3
<211> LENGTH: 1215
<212> TYPE: DNA
<213> ORGANISM: Saccharomyces cerevisiae

<400> SEQUENCE: 3

| | | |
|---|---|---|
| atgtctgaaa atcaacgttt aggattatca gaggaagagg tagaagcggc tgaagtactt | 60 |
| ggggtgttga acaatcatg cagacagaag tcgcagcctt cagaggacgt ctcacaagct | 120 |
| gacaaaatgc cggcaagtga gtcgtctacg acgccgctaa acattttgga tcgcgtaagt | 180 |

```
aacaaaatta tcagtaacgt agtgacattc tacgatgaaa taaacaccaa caagaggcca        240
ctgaaatcaa tagggaggct gctagacgat gacgatgacg agcatgatga ttacgactac        300
aacgacgatg agttcttcac caacaagaga cagaagctgt cgcgggcgat tgccaagggg        360
aaggacaact tgaaagagta caagctgaac atgtccatcg agtctaagaa gaggcttgta        420
acgtgcttgc atcttttaaa gctggccaat aagcagcttt ccgataaaat ctcgtgttta        480
caggaccttg ttgaaaagga gcaggtgcat cctttgcaca agcaagatgg aaatgctagg        540
acgaccactg gagctggcga ggacgagaca tcgtcagacg aagacgacga cgatgaggag        600 tttttgatg cctcagagca ggtcaacgcc agcgagcagt ctattgtggt gaaaatggag         660
gtggtcggca cagtcaagaa agtctactcg ctgatatcga agttcacagc aaattcgctg        720
ccggagcccg caagatctca ggttcgggaa agtcttctaa acttaccac aaattggttc         780 gacagcgtcc acagtacatc actgccgcat catgcttcgt ttcattatgc caactgtgaa        840
gaacaaaaag tggagcaaca gcaacagcaa cagcaacagc agcagcagca gcaacttttg        900
cagcagcaac tcctgcaaca gcaacagcaa aaaaggaaca aggatggcga cgactcagcc        960
tcgccgtcct cctccgtaac tgcgaatggg aaagtactca ttctcgccaa gaatccctg        1020 gaaatggtga gaaatgtcat gggcgtagtc gactccacgt tgggcaaggc tgaagaatgg       1080
gtgaagcaga acaggaggt aaaagaaatg atcagggagc gtttcttgca acagcagcaa        1140
cagtacaggc agcaacagca gaaggatggc aattacgtaa agccctctca ggacaacgtg       1200
gatagcaagg actaa                                                        1215
```

<210> SEQ ID NO 4
<211> LENGTH: 769
<212> TYPE: PRT
<213> ORGANISM: Panax ginseng

<400> SEQUENCE: 4

```
Met Trp Lys Gln Lys Gly Ala Gln Gly Asn Asp Pro Tyr Leu Tyr Ser
 1               5                   10                  15

Thr Asn Asn Phe Val Gly Arg Gln Tyr Trp Glu Phe Gln Pro Asp Ala
            20                  25                  30

Gly Thr Pro Glu Glu Arg Glu Val Glu Lys Ala Arg Lys Asp Tyr
        35                  40                  45

Val Asn Asn Lys Lys Leu His Gly Ile His Pro Cys Ser Asp Met Leu
    50                  55                  60

Met Arg Arg Gln Leu Ile Lys Glu Ser Gly Ile Asp Leu Leu Ser Ile
65                  70                  75                  80

Pro Pro Leu Arg Leu Asp Glu Asn Glu Gln Val Asn Tyr Asp Ala Val
                85                  90                  95

Thr Thr Ala Val Lys Lys Ala Leu Arg Leu Asn Arg Ala Ile Gln Ala
            100                 105                 110

His Asp Gly His Trp Pro Ala Glu Asn Ala Gly Ser Leu Leu Tyr Thr
        115                 120                 125

Pro Pro Leu Ile Ile Ala Leu Tyr Ile Ser Gly Thr Ile Asp Thr Ile
    130                 135                 140

Leu Thr Lys Gln His Lys Lys Glu Leu Ile Arg Phe Val Tyr Asn His
145                 150                 155                 160

Gln Asn Glu Asp Gly Gly Trp Gly Ser Tyr Ile Glu Gly His Ser Thr
                165                 170                 175

Met Ile Gly Ser Val Leu Ser Tyr Val Met Leu Arg Leu Leu Gly Glu
```

```
            180             185             190
Gly Leu Ala Glu Ser Asp Asp Gly Asn Gly Ala Val Glu Arg Gly Arg
            195             200             205
Lys Trp Ile Leu Asp His Gly Ala Ala Gly Ile Pro Ser Trp Gly
210             215             220
Lys Thr Tyr Leu Ala Val Leu Gly Val Tyr Glu Trp Gly Cys Asn
225             230             235             240
Pro Leu Pro Pro Glu Phe Trp Leu Phe Pro Ser Ser Phe Pro Phe His
            245             250             255
Pro Ala Lys Met Trp Ile Tyr Cys Arg Cys Thr Tyr Met Pro Met Ser
            260             265             270
Tyr Leu Tyr Gly Lys Arg Tyr His Gly Pro Ile Thr Asp Leu Val Leu
            275             280             285
Ser Leu Arg Gln Glu Ile Tyr Asn Ile Pro Tyr Glu Gln Ile Lys Trp
            290             295             300
Asn Gln Gln Arg His Asn Cys Cys Lys Glu Asp Leu Tyr Tyr Pro His
305             310             315             320
Thr Leu Val Gln Asp Leu Val Trp Asp Gly Leu His Tyr Phe Ser Glu
            325             330             335
Pro Phe Leu Lys Arg Trp Pro Phe Asn Lys Leu Arg Lys Arg Gly Leu
            340             345             350
Lys Arg Val Val Glu Leu Met Arg Tyr Gly Ala Thr Glu Thr Arg Phe
            355             360             365
Ile Thr Thr Gly Asn Gly Glu Lys Ala Leu Gln Ile Met Ser Trp Trp
            370             375             380
Ala Glu Asp Pro Asn Gly Asp Glu Phe Lys His His Leu Ala Arg Ile
385             390             395             400
Pro Asp Phe Leu Trp Ile Ala Glu Asp Gly Met Thr Val Gln Ser Phe
            405             410             415
Gly Ser Gln Leu Trp Asp Cys Ile Leu Ala Thr Gln Ala Ile Ile Ala
            420             425             430
Thr Asn Met Val Glu Glu Tyr Gly Asp Ser Leu Lys Lys Ala His Phe
            435             440             445
Phe Ile Lys Glu Ser Gln Ile Lys Glu Asn Pro Arg Gly Asp Phe Leu
450             455             460
Lys Met Cys Arg Gln Phe Thr Lys Gly Ala Trp Thr Phe Ser Asp Gln
465             470             475             480
Asp His Gly Cys Val Val Ser Asp Cys Thr Ala Glu Ala Leu Lys Cys
            485             490             495
Leu Leu Leu Leu Ser Gln Met Pro Gln Asp Ile Val Gly Glu Lys Pro
            500             505             510
Glu Val Glu Arg Leu Tyr Glu Ala Val Asn Val Leu Tyr Leu Gln
            515             520             525
Ser Arg Val Ser Gly Gly Phe Ala Val Trp Glu Pro Pro Val Pro Lys
            530             535             540
Pro Tyr Leu Glu Met Leu Asn Pro Ser Glu Ile Phe Ala Asp Ile Val
545             550             555             560
Val Glu Arg Glu His Ile Glu Cys Thr Ala Ser Val Ile Lys Gly Leu
            565             570             575
Met Ala Phe Lys Cys Leu His Pro Gly His Arg Gln Lys Glu Ile Glu
            580             585             590
Asp Ser Val Ala Lys Ala Ile Arg Tyr Leu Glu Arg Asn Gln Met Pro
            595             600             605
```

```
Asp Gly Ser Trp Tyr Gly Phe Trp Gly Ile Cys Phe Leu Tyr Gly Thr
    610                 615                 620

Phe Phe Thr Leu Ser Gly Phe Ala Ser Ala Gly Arg Thr Tyr Asp Asn
625                 630                 635                 640

Ser Glu Ala Val Arg Lys Gly Val Lys Phe Phe Leu Ser Thr Gln Asn
                645                 650                 655

Glu Glu Gly Gly Trp Gly Glu Ser Leu Glu Ser Cys Pro Ser Glu Lys
                660                 665                 670

Phe Thr Pro Leu Lys Gly Asn Arg Thr Asn Leu Val Gln Thr Ser Trp
            675                 680                 685

Ala Met Leu Gly Leu Met Phe Gly Gly Gln Ala Glu Arg Asp Pro Thr
    690                 695                 700

Pro Leu His Arg Ala Ala Lys Leu Leu Ile Asn Ala Gln Met Asp Asn
705                 710                 715                 720

Gly Asp Phe Pro Gln Gln Glu Ile Thr Gly Val Tyr Cys Lys Asn Ser
                725                 730                 735

Met Leu His Tyr Ala Glu Tyr Arg Asn Ile Phe Pro Leu Trp Ala Leu
            740                 745                 750

Gly Glu Tyr Arg Lys Arg Val Trp Leu Pro Lys His Gln Gln Leu Lys
            755                 760                 765

Ile

<210> SEQ ID NO 5
<211> LENGTH: 482
<212> TYPE: PRT
<213> ORGANISM: Panax ginseng

<400> SEQUENCE: 5

Met Val Leu Phe Phe Ser Leu Ser Leu Leu Leu Pro Leu Leu Leu
1               5                   10                  15

Leu Phe Ala Tyr Phe Ser Tyr Thr Lys Arg Ile Pro Gln Lys Glu Asn
            20                  25                  30

Asp Ser Lys Ala Pro Leu Pro Pro Gly Gln Thr Gly Trp Pro Leu Ile
        35                  40                  45

Gly Glu Thr Leu Asn Tyr Leu Ser Cys Val Lys Ser Gly Val Ser Glu
    50                  55                  60

Asn Phe Val Lys Tyr Arg Lys Glu Lys Tyr Ser Pro Lys Val Phe Arg
65                  70                  75                  80

Thr Ser Leu Leu Gly Glu Pro Met Ala Ile Leu Cys Gly Pro Glu Gly
                85                  90                  95

Asn Lys Phe Leu Tyr Ser Thr Glu Lys Lys Leu Val Gln Val Trp Phe
            100                 105                 110

Pro Ser Ser Val Glu Lys Met Phe Pro Arg Ser His Gly Glu Ser Asn
        115                 120                 125

Ala Asp Asn Phe Ser Lys Val Arg Gly Lys Met Met Phe Leu Leu Lys
    130                 135                 140

Val Asp Gly Met Lys Lys Tyr Val Gly Leu Met Asp Arg Val Met Lys
145                 150                 155                 160

Gln Phe Leu Glu Thr Asp Trp Asn Arg Gln Gln Ile Asn Val His
                165                 170                 175

Asn Thr Val Lys Lys Tyr Thr Val Thr Met Ser Cys Arg Val Phe Met
            180                 185                 190

Ser Ile Asp Asp Glu Glu Gln Val Thr Arg Leu Gly Ser Ser Ile Gln
        195                 200                 205
```

-continued

Asn Ile Glu Ala Gly Leu Leu Ala Val Pro Ile Asn Ile Pro Gly Thr
210                 215                 220

Ala Met Asn Arg Ala Ile Lys Thr Val Lys Leu Leu Thr Arg Glu Val
225                 230                 235                 240

Glu Ala Val Ile Lys Gln Arg Lys Val Asp Leu Leu Glu Asn Lys Gln
            245                 250                 255

Ala Ser Gln Pro Gln Asp Leu Leu Ser His Leu Leu Leu Thr Ala Asn
        260                 265                 270

Gln Asp Gly Gln Phe Leu Ser Glu Ser Asp Ile Ala Ser His Leu Ile
    275                 280                 285

Gly Leu Met Gln Gly Gly Tyr Thr Thr Leu Asn Gly Thr Ile Thr Phe
290                 295                 300

Val Leu Asn Tyr Leu Ala Glu Phe Pro Asp Val Tyr Asn Gln Val Leu
305                 310                 315                 320

Lys Glu Gln Val Glu Ile Ala Asn Ser Lys His Pro Lys Glu Leu Leu
            325                 330                 335

Asn Trp Glu Asp Leu Arg Lys Met Lys Tyr Ser Trp Asn Val Ala Gln
        340                 345                 350

Glu Val Leu Arg Ile Ile Pro Pro Gly Val Gly Thr Phe Arg Glu Ala
    355                 360                 365

Ile Thr Asp Phe Thr Tyr Ala Gly Tyr Leu Ile Pro Lys Gly Trp Lys
370                 375                 380

Met His Leu Ile Pro His Asp Thr His Lys Asn Pro Thr Tyr Phe Pro
385                 390                 395                 400

Ser Pro Glu Lys Phe Asp Pro Thr Arg Phe Glu Gly Asn Gly Pro Ala
            405                 410                 415

Pro Tyr Thr Phe Thr Pro Phe Gly Gly Gly Pro Arg Met Cys Pro Gly
        420                 425                 430

Ile Glu Tyr Ala Arg Leu Val Ile Leu Ile Phe Met His Asn Val Val
    435                 440                 445

Thr Asn Phe Arg Trp Glu Lys Leu Ile Pro Asn Glu Lys Ile Leu Thr
450                 455                 460

Asp Pro Ile Pro Arg Phe Ala His Gly Leu Pro Ile His Leu His Pro
465                 470                 475                 480

His Asn

<210> SEQ ID NO 6
<211> LENGTH: 709
<212> TYPE: PRT
<213> ORGANISM: Panax ginseng

<400> SEQUENCE: 6

Met Leu Lys Val Ser Pro Phe Asp Leu Met Thr Glu Ile Leu Arg Gly
1               5                   10                  15

Gly Ser Ile Asp Pro Pro Asn Ser Ser Val Ser Ala Ala Gly Ala Ser
            20                  25                  30

Met Gln Pro Ser Leu Ala Met Leu Val Val Asn Arg Glu Leu Leu Met
        35                  40                  45

Leu Leu Thr Thr Ser Val Ala Val Leu Ile Gly Cys Val Val Val Leu
    50                  55                  60

Val Trp Arg Lys Ser Ser Ser Gln Lys His Ala Lys Ser Phe Glu Ala
65                  70                  75                  80

Pro Lys Leu Leu Ile Pro Lys Ile Glu Pro Glu Glu Val Val Asp Asp
                85                  90                  95

```
Gly Lys Lys Lys Val Thr Ile Phe Phe Gly Thr Gln Thr Gly Thr Ala
            100                 105                 110
Glu Gly Phe Ala Lys Ala Leu Ala Glu Glu Ala Lys Ala Arg Tyr Glu
        115                 120                 125
Lys Ala Ile Phe Lys Val Ile Asp Leu Asp Asp Tyr Ala Pro Glu Asp
130                 135                 140
Asp Asp Tyr Glu Thr Lys Leu Lys Lys Glu Ser Leu Ala Phe Phe Phe
145                 150                 155                 160
Leu Ala Thr Tyr Gly Asp Gly Glu Pro Thr Asp Asn Ala Ala Arg Phe
                165                 170                 175
Tyr Lys Trp Phe Thr Glu Gly Lys Glu Lys Arg Glu Trp Leu Asn Asn
            180                 185                 190
Leu Gln Tyr Gly Val Phe Gly Leu Gly Asn Arg Gln Tyr Glu His Phe
        195                 200                 205
Asn Lys Ile Ala Lys Val Val Asp Asp Gly Leu Ala Glu Gln Gly Ala
        210                 215                 220
Lys Arg Leu Val Pro Val Gly Met Gly Asp Asp Gln Cys Ile Glu
225                 230                 235                 240
Asp Asp Phe Thr Ala Trp Arg Glu Leu Val Trp Pro Glu Leu Asp Gln
                245                 250                 255
Leu Leu Leu Asp Glu Glu Asp Thr Ala Ala Ala Thr Pro Tyr Thr Ala
            260                 265                 270
Ala Val Leu Glu Tyr Arg Val Val Phe His Asp Arg Thr Asp Ser Ser
        275                 280                 285
Thr Leu Leu Asn Gly Thr Thr Ser Val Ser Asn Gly His Ala Phe Tyr
        290                 295                 300
Asp Ala Gln His Pro Cys Arg Ala Asn Val Ala Val Lys Arg Glu Leu
305                 310                 315                 320
His Thr Leu Glu Ser Asp Arg Ser Cys Thr His Leu Glu Phe Asp Ile
                325                 330                 335
Ser Ser Thr Gly Leu Ala Tyr Glu Thr Gly Asp His Val Gly Val Tyr
            340                 345                 350
Thr Glu Asn Leu Ile Glu Ile Val Glu Glu Ala Glu Arg Leu Leu Ala
        355                 360                 365
Ile Ser Pro Asp Thr Tyr Phe Ser Ile His Thr Glu Lys Glu Asp Gly
        370                 375                 380
Ser Pro Val Ser Gly Ser Ser Leu Gln Pro Pro Phe Pro Pro Cys Thr
385                 390                 395                 400
Leu Arg Glu Ala Leu Arg Arg Tyr Ala Asp Leu Leu Ser Ser Pro Lys
                405                 410                 415
Lys Ser Ala Leu Leu Ala Leu Ala Ala His Ala Ser Asp Pro Ser Glu
            420                 425                 430
Ala Asp Arg Leu Arg Phe Leu Ala Ser Pro Ala Gly Lys Asp Glu Tyr
        435                 440                 445
Ala Gln Trp Ile Val Ala Asn Gln Arg Ser Leu Leu Glu Val Leu Ala
        450                 455                 460
Glu Phe Pro Ser Ala Lys Pro Pro Leu Gly Val Phe Phe Ala Ser Val
465                 470                 475                 480
Ala Pro Arg Leu Gln Pro Arg Tyr Tyr Ser Ile Ser Ser Ser Pro Arg
                485                 490                 495
Met Ala Pro Ser Arg Ile His Val Thr Cys Ala Leu Val Phe Glu Arg
            500                 505                 510
```

```
Thr Pro Ala Gly Arg Ile His Lys Gly Val Cys Ser Thr Trp Met Lys
            515                 520                 525

Asn Ala Val Ser Leu Glu Glu Gly Asn Asp Cys Ser Arg Ala Pro Ile
530                 535                 540

Phe Val Arg Gln Ser Asn Phe Lys Leu Pro Ser Asp Ser Arg Met Pro
545                 550                 555                 560

Ile Ile Met Ile Gly Pro Gly Thr Gly Leu Ala Pro Phe Arg Gly Phe
                565                 570                 575

Leu Gln Glu Arg Leu Ala Leu Lys Glu Ala Gly Ala Glu Leu Gly Pro
            580                 585                 590

Ala Val Leu Tyr Phe Gly Cys Arg Asn Arg Lys Leu Asp Phe Ile Tyr
            595                 600                 605

Glu Asp Glu Leu Asn Asn Phe Val Glu Ser Gly Ala Ile Ser Glu Met
610                 615                 620

Val Val Ala Phe Ser Arg Glu Gly Pro Thr Lys Glu Tyr Val Gln His
625                 630                 635                 640

Lys Met Ser Gln Lys Ala Ser Glu Ile Trp Asn Met Ile Ser Glu Gly
                645                 650                 655

Ala Tyr Ile Tyr Val Cys Gly Asp Ala Lys Gly Met Ala Arg Asp Val
            660                 665                 670

His Arg Thr Leu His Thr Ile Ala Gln Glu Gln Gly Ala Leu Asp Ser
            675                 680                 685

Ser Lys Ala Glu Ser Leu Val Lys Asn Leu Gln Met Thr Gly Arg Tyr
            690                 695                 700

Leu Arg Asp Val Trp
705

<210> SEQ ID NO 7
<211> LENGTH: 527
<212> TYPE: PRT
<213> ORGANISM: Saccharomyces cerevisiae

<400> SEQUENCE: 7

Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
            115                 120                 125

Leu Ala Glu Ala Pro Val Leu Ala Ser Asp Arg Leu Pro Tyr Lys Asn
        130                 135                 140

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
                165                 170                 175
```

```
Thr Ser Tyr His Ile Pro Met Ala Thr Thr Glu Gly Cys Leu Val Ala
        180                 185                 190

Ser Ala Met Arg Gly Cys Lys Ala Ile Asn Ala Gly Gly Ala Thr
        195                 200             205

Thr Val Leu Thr Lys Asp Gly Met Thr Arg Gly Pro Val Val Arg Phe
    210                 215                 220

Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
                245                 250                 255

Ala Arg Leu Gln His Ile Gln Thr Cys Leu Ala Gly Asp Leu Leu Phe
        260                 265                 270

Met Arg Phe Arg Thr Thr Thr Gly Asp Ala Met Gly Met Asn Met Ile
        275                 280                 285

Ser Lys Gly Val Glu Tyr Ser Leu Lys Gln Met Val Glu Glu Tyr Gly
        290                 295                 300

Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                325                 330                 335

Val Ala Glu Ala Thr Ile Pro Gly Asp Val Val Arg Lys Val Leu Lys
        340                 345                 350

Ser Asp Val Ser Ala Leu Val Glu Leu Asn Ile Ala Lys Asn Leu Val
        355                 360                 365

Gly Ser Ala Met Ala Gly Ser Val Gly Gly Phe Asn Ala His Ala Ala
        370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                405                 410                 415

Asp Leu Arg Ile Ser Val Ser Met Pro Ser Ile Glu Val Gly Thr Ile
        420                 425                 430

Gly Gly Gly Thr Val Leu Glu Pro Gln Gly Ala Met Leu Asp Leu Leu
        435                 440                 445

Gly Val Arg Gly Pro His Ala Thr Ala Pro Gly Thr Asn Ala Arg Gln
        450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                485                 490                 495

Asn Arg Lys Pro Ala Glu Pro Thr Lys Pro Asn Asn Leu Asp Ala Thr
        500                 505                 510

Asp Ile Asn Arg Leu Lys Asp Gly Ser Val Thr Cys Ile Lys Ser
        515                 520                 525

<210> SEQ ID NO 8
<211> LENGTH: 545
<212> TYPE: PRT
<213> ORGANISM: Panax ginseng

<400> SEQUENCE: 8

Met Glu Leu Glu Arg Ser Tyr Arg Glu Asn Asp Glu Tyr Phe Leu Met
1               5                   10                  15

Phe Ala Ala Thr Leu Leu Phe Gly Phe Val Leu Tyr Leu Phe Thr Leu
```

-continued

```
                20                  25                  30
Arg Arg Arg Arg Arg Arg Glu Lys Lys Gly Gly Ala Gly Ser Met
                35                  40                  45
Glu Ile Ile Asn Gly Ala Tyr Lys Met Thr Ser Ser Ser Glu Val Asn
50                  55                  60
Gly His Cys Thr Pro Glu Asp Ile Ala Gly Ser Ser Asp Asp Val Ile
65                  70                  75                  80
Ile Val Gly Ala Gly Val Ala Gly Ser Ala Leu Ala Tyr Thr Leu Ala
                85                  90                  95
Lys Asp Gly Arg Arg Val His Val Ile Glu Arg Asp Leu Thr Glu Gln
                100                 105                 110
Asp Arg Ile Val Gly Glu Leu Leu Gln Pro Gly Gly Tyr Leu Lys Leu
            115                 120                 125
Val Glu Leu Gly Leu Glu Asp Cys Val Asn Glu Ile Asp Ala Gln Arg
            130                 135                 140
Val Phe Gly Tyr Ala Leu Tyr Met Asp Gly Lys Asn Thr Arg Leu Ser
145                 150                 155                 160
Tyr Pro Leu Glu Lys Phe His Ala Asp Val Ala Gly Arg Ser Phe His
                165                 170                 175
Asn Gly Arg Phe Ile Gln Arg Met Arg Glu Lys Ala Ala Ser Leu Pro
            180                 185                 190
Asn Val Arg Met Glu Gln Gly Thr Val Thr Ser Leu Val Glu Gln Lys
            195                 200                 205
Gly Thr Val Lys Gly Val Arg Tyr Lys Thr Lys Asn Gly Gln Glu Met
            210                 215                 220
Ser Ala Ala Tyr Ala Pro Leu Thr Ile Val Cys Asp Gly Cys Phe Ser
225                 230                 235                 240
Asn Leu Arg His Ser Leu Cys Asn Pro Lys Val Asp Val Pro Ser Cys
                245                 250                 255
Phe Val Gly Leu Ile Leu Glu Asn Ile Asp Leu Pro His Ile Asn His
            260                 265                 270
Gly His Val Ile Leu Ala Asp Pro Ser Pro Ile Leu Phe Tyr Lys Ile
            275                 280                 285
Ser Ser Thr Glu Ile Arg Cys Leu Val Asp Val Pro Gly Gln Lys Val
290                 295                 300
Pro Ser Ile Ala Asn Gly Glu Leu Ala His Tyr Leu Lys Thr Ser Val
305                 310                 315                 320
Ala Pro Gln Ile Pro Pro Glu Leu Tyr Lys Ser Phe Ile Ala Ala Ile
                325                 330                 335
Asp Lys Gly Lys Ile Lys Thr Met Pro Asn Arg Ser Met Pro Ala Asp
            340                 345                 350
Pro His Ser Thr Pro Gly Ala Leu Leu Leu Gly Asp Ala Phe Asn Met
            355                 360                 365
Arg His Pro Leu Thr Gly Gly Gly Met Thr Val Ala Leu Ser Asp Ile
            370                 375                 380
Val Leu Ile Arg Asp Leu Leu Arg Pro Leu Arg Asp Leu His Asp Ser
385                 390                 395                 400
Ser Thr Leu Cys Lys Tyr Leu Glu Ser Phe Tyr Thr Leu Arg Lys Pro
                405                 410                 415
Val Ala Ser Thr Ile Asn Thr Leu Ala Gly Ala Leu Tyr Lys Val Phe
            420                 425                 430
Cys Ala Ser Pro Asp Lys Ala Arg Gln Glu Met Arg Asp Ala Cys Phe
            435                 440                 445
```

Asp Tyr Leu Ser Leu Gly Gly Ile Cys Ser Glu Gly Pro Ile Ala Leu
    450                 455                 460

Leu Ser Gly Leu Asn Pro Arg Pro Met Ser Leu Phe Phe His Phe
465                 470                 475                 480

Ala Val Ala Ile Tyr Gly Val Gly Arg Leu Leu Ile Pro Phe Pro Ser
                485                 490                 495

Pro Arg Lys Met Trp Leu Gly Ala Arg Leu Ile Ser Gly Ala Ser Gly
            500                 505                 510

Ile Ile Phe Pro Ile Ile Lys Ser Glu Gly Val Arg Gln Met Phe Phe
        515                 520                 525

Pro Ala Thr Val Pro Ala Tyr Tyr Arg Ala Pro Pro Ile Thr Lys Lys
    530                 535                 540

Met
545

<210> SEQ ID NO 9
<211> LENGTH: 29
<212> TYPE: DNA
<213> ORGANISM: Artificial Sequence
<220> FEATURE:
<223> OTHER INFORMATION: Synthetic oligonucleotide (PGK pro F)

<400> SEQUENCE: 9
cgagctcaga cgcgaattt tcgaagaag        29

<210> SEQ ID NO 10
<211> LENGTH: 51
<212> TYPE: DNA
<213> ORGANISM: Artificial Sequence
<220> FEATURE:
<223> OTHER INFORMATION: Synthetic oligonucleotide (PGK pro F)

<400> SEQUENCE: 10
gactagttct agatgtttta tatttgttgt aaaaagtaga taattacttc c        51

<210> SEQ ID NO 11
<211> LENGTH: 70
<212> TYPE: DNA
<213> ORGANISM: Artificial Sequence
<220> FEATURE:
<223> OTHER INFORMATION: Synthetic oligonucleotide (P_INO2 F)

<400> SEQUENCE: 11
catttagcag cgccagcgcc cttctaagct cttccatacc tatacgcatg aggtttcccg        60
actggaaagc        70

<210> SEQ ID NO 12
<211> LENGTH: 80
<212> TYPE: DNA
<213> ORGANISM: Artificial sequence
<220> FEATURE:
<223> OTHER INFORMATION: Synthetic oligonucleotide (P_INO2 R)

<400> SEQUENCE: 12
ttatccagat ctaggatacc cagtaattcg ttcccagttg cttgttgcat tgttttatat        60
ttgttgtaaa aagtagataa        80

<210> SEQ ID NO 13
<211> LENGTH: 70
<212> TYPE: DNA
<213> ORGANISM: Artificial Sequence

```
<220> FEATURE:
<223> OTHER INFORMATION: Synthetic oligonucleotide (P_INO4 F)

<400> SEQUENCE: 13
aaaaatgaat ccgggatatt caattctagg aacctcgaac tatattgcat aggtttcccg      60
actggaaagc                                                             70

<210> SEQ ID NO 14
<211> LENGTH: 80
<212> TYPE: DNA
<213> ORGANISM: Artificial Sequence
<220> FEATURE:
<223> OTHER INFORMATION: Synthetic oligonucleotide (P_INO4 R)

<400> SEQUENCE: 14
tcggacaatc ccggctgtat tgtttgtatc tccttaatat cgttcgtcat tgttttatat      60
ttgttgtaaa aagtagataa                                                  80

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide (INO2 to PGK1 F)

<400> SEQUENCE: 15
gcgcccttct aagctcttcc                                                  20

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide (INO2 to PGK1 R)

<400> SEQUENCE: 16
acccagtaat tcgttcccag ttg                                              23

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide (INO4 to PGK1 F)

<400> SEQUENCE: 17
ccgggatatt caattctagg aacct                                            25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide (INO4 to PGK1 R)

<400> SEQUENCE: 18
tttcttcaca ttagccagtt caccc                                            25

<210> SEQ ID NO 19
<211> LENGTH: 70
<212> TYPE: DNA
<213> ORGANISM: Artificial Sequence
<220> FEATURE:
<223> OTHER INFORMATION: Synthetic oligonucleotide (Del OPI1 F)
```

```
<400> SEQUENCE: 19
ttaaagcgtg tgtatcagga cagtgttttt aacgaagata ctagtcattg ccagtcacga    60
cgttgtaaaa                                                            70

<210> SEQ ID NO 20
<211> LENGTH: 70
<212> TYPE: DNA
<213> ORGANISM: Artificial Sequence
<220> FEATURE:
<223> OTHER INFORMATION: Synthetic oligonucleotide (Del OPI1 R)

<400> SEQUENCE: 20
tataatatta ttactggtgg taatgcatga aagacctcaa tctgtctcgg aggtttcccg    60
actggaaagc                                                            70

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide (OPI1 F)

<400> SEQUENCE: 21
gcgtgtgtat caggacagtg t                                               21

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide (OPI1 R)

<400> SEQUENCE: 22
ctggtggtaa tgcatgaaag acctc                                           25
```

INCREASED PRODUCTION OF GINSENOSIDES THROUGH YEAST CELL ORGANELLE IMPROVEMENT

This application is a division of U.S. application Ser. No. 15/880,838, filed Jan. 26, 2018, the entirety of which is incorporated herein by reference. U.S. application Ser. No. 15/880,838, filed Jan. 26, 2018, also claims priority to Korean Application No. 10-2017-0056258, filed May 2, 2017.

BACKGROUND OF THE INVENTION

1. Field of the Invention

The present invention relates to a recombinant yeast for enhancing ginsenoside production, and a method of producing ginsenoside by using the same.

2. Description of the Related Art

Saponins, glycosides widely distributed in the plant kingdom, refer to substances composed of diverse ring compounds formed by the non-sugar portion thereof. Triterpene saponin, which is a saponin contained in ginseng or red ginseng as a major physiologically active ingredient, is named ginsenoside, which means ginseng glycoside, to distinguish it from other vegetables' saponin based on a different chemical structure.

Ginsenosides are classified into three groups based on their aglycone structure: protopanaxadiol-type (PPD-type) ginsenosides, protopanaxatriol-type (PPT-type) ginsenosides, and oleanolic acid-type ginsenosides. These three groups are further classified based on the position and number of sugar moieties (aglycones) attached by a glycosidic bond at the C-3, C-6, and C-20 positions of the rings in the chemical structure. The oleanolic acid-type ginsenoside has a pentacyciic backbone and ginsenoside Ro is the only saponin having oleanolic acid as aglycone. To date, more than 40 ginsenosides have been isolated, and most of them are PPD-type ginsenosides. PPD-type ginsenosides include Rb1, Rb2, Rb3, Rc, Rd, Gypenoside XVII, Compound O, Compound Mc1, F2, Compound Y, Compound Mc, Rg3, Rh2, and C-K. PPT-type ginsenosides include Re, Rg1, Rf, Rg2, Rh1, etc.

It is known that a representative pharmacological effect of ginseng is attributed to ginsenosides, and up to now, about 30 different kinds of ginsenosides have been isolated from ginseng and ginseng products (Shibata, 2001), and reported to have different pharmacological actions such as anti-diabetic activity, anti-inflammatory action, anti-aging action, anti-cancer action, etc. In addition to ginsencsides, phenolic compounds, polyacetylenes, alkaloids, and polysaccharides are known as other physiologically active ingredients. More than 10 kinds of antioxidative phenolic substances are revealed as an active ingredient for anti-aging, and they are also known to have physiological activities such as hypertension-inhibitory activity, anticancer activity, antioxidant activity, whitening activity, etc. Anti-stress effect that nonspecifically maintains physical and mental stability against various stresses is also reported in recent studies (Lee et. al., 2008).

Worldwide, ginseng is commercially cultivated in Korea, China, Japan, the United States, Canada, Europe, etc. By the end of 1980, about 46% of all ginsengs produced in the world had been produced in Korea. However, Korea's market share decreased to about 39% in the 1990s, and China accounted for more than 50%. American ginseng of the United States and Canada accounted for 10%. Recently, Korean ginseng have rapidly decreased in share of the world market. One of the biggest reasons is that Korean ginseng is very excellent in its efficacy, but it is very weak in price competitiveness. Since Korean ginseng has very excellent characteristics and advantages, there is an urgent need for efforts to improve international competitiveness of ginseng products against the current rapidly changing world situation and WTO, major investment in bio-industry and economic crisis.

Pharmacological studies of ginseng have increased interest in ginsenoside which is a ginseng saponin component, and there is a growing need for their mass-production. However, mass-production of useful substance of ginseng through general cultivation methods includes problems such as a long growing period of 4-6 years, difficulty in pest control due to shading culture, rotation agriculture, etc., and therefore, development of a new alternative production method is urgently required.

Recently, a large number of ginseng saponin-related genes have been identified on the basis of biotechnology, and development of a technology for mass-production of ginsenoside in yeast by using these genes has been receiving attention. Since ginsenoside is biosynthesized via an isoprenoid synthetic pathway including a mevalonic acid biosynthetic pathway in plants (Cristensen, 2008), synthetic biology studies have been attempted to develop ginsenoside-producing strains by redesigning an ergosterol biosynthetic pathway in yeast. Recently, China's Huang and Zhang joint research team reported that protopanaxadiol dammarenediol-II synthase and protopanaxadiol synthase genes of ginseng, together with a NADPH-cytochrome P450 reductase gene of *Arabidopsis thaliana*, were introduced into yeast *Saccharomyces cerevisiae*, resulting in successful production of protopanaxadiol. They increased squalene and 2,3-oxidosqualene supplies through overexpressing tHMG1 which is an N-terminal HMG gene, and they also amplified precursor supply for protopanaxadiol production by overexpressing FPP synthase gene (ERG20), squalene synthase gene (EFG9), and 2,3-oxidosqualene synthase gene (ERG1) at the same time. Further, conversion efficiency of protopanaxadiol was further increased by synthesis of protopanaxadiol synthase gene through yeast codon optimization. Finally, a ginsenoside biosynthetic pathway was completed by introduction of uridin diphosphate glycosyltransferase gene. (Dai et al., 2013). It is expected that the ginsenoside-producing synthetic yeast may serve as the basis for creating an economic alternative way for production of ginsenosides in place of a complex process of extraction from plant sources.

Under this background, the present inventors have made many efforts to improve ginsenoside production by using a yeast. As a result, they developed a recombinant yeast in which expressions of genes improving a cell organelle of a ginsenoside-producing yeast is controlled, and a method of preparing the recombinant yeast, and they found that the recombinant yeast shows increased production of protopanaxadioi which is an intermediate product in ginsenoside biosynthesis, as compared with a known yeast having ability to produce ginsenoside, thereby completing the present invention.

SUMMARY OF THE INVENTION

An object of the present invention is to provide a recombinant yeast for producing ginsenoside or a precursor thereof.

Another object of the present invention is to provide a method of preparing the recombinant yeast.

Still another object of the present invention is to provide a method of producing ginsenoside or a precursor thereof with a high yield by using the recombinant yeast.

BRIEF DESCRIPTION OF THE DRAWINGS

FIG. 1 is a schematic illustration showing regulation of phospholipid biosynthesis-related genes by transcription factors, INO2, INO4, and OPI1 and intracellular functions related thereto;

FIG. 2 shows a ginsenoside biosynthesis metabolic pathway;

FIG. 3 is a vector map of pUC57-URA3HA-PGK1 which is a vector for overexpressing INO2 or INO4 gene; and FIG. 4 is a graph showing comparison of production of squalene, 2,3-oxidosqualene, and protopanaxadiol between INO2 or INO4 overexpression or OPI1 deletion and a control group.

DETAILED DESCRIPTION OF THE PREFERRED EMBODIMENTS

The present invention will be described in detail as follows. Meanwhile, each description and embodiment disclosed in this application may be applied to other descriptions and embodiments. That is, all combinations of various elements disclosed in this application fall within the scope of the present application. Further, the scope of the present application is not limited by the specific description described below.

An aspect to achieve the objects of the present invention provides a recombinant yeast for producing ginsenoside or a precursor thereof, in which an expression level of a transcription factor of a phospholipid biosynthetic gene is changed, as compared with an intrinsic expression level.

The present invention is characterized in that among yeast cell's organelles, endoplasmic reticulum (ER) which functions in protein synthesis, formation of a secondary structure of proteins, and transport of proteins to the intracellular position responsible for each function is improved to increase the space of endoplasmic reticulum or to control a membrane composition and a stress response against unfolded proteins, thereby increasing production of ginsenoside or a precursor thereof.

In the present invention, expressions of genes involved in phospholipid biosynthesis are regulated, and specifically, expression levels of transcription factors regulating expressions of the genes involved in phospholipid biosynthesis are changed, in order to improve the endoplasmic reticulum of the yeast. More specifically, transcription factors of the genes involved in phospholipid biosynthesis may be one or more selected from the group consisting of INO2, INO4, and OPI1.

As used herein, the term "INO2 (INOsitol requiring 2)" and "INO4 (INOsitol requiring 4)" are transcription factors that regulate expressions of 70 or more genes responsible for various functions such as formation of protein structures, including genes involved in phospholipid biosynthesis. Overexpression of the transcription factors increases expressions of the genes involved in phospholipid biosynthesis, thereby increasing the size of endoplasmic reticulum, controlling cell membrane components, and inducing stress responses against unfolded proteins. INO2 and INO4 are transcription factors that function as a complex, but unlike INO4, INO2 was reported to plays a critical role in transcriptional regulation (Influence of gene dosage and autoregulation of the regulatory genes INO2 and INO4 on inositol/choline-repressible gene transcription in the yeast *Saccharomyces cerevisiae*. Curr Genet. 1997 June; 31(6): 462-8. Schwank S, Hoffmann B, Sch-uller H J.).

Information of INO2 and a gene encoding INO2 may be obtained from database such as GenBank at US NIH, and for example, the INO2 gene may have a nucleotide sequence of SEQ ID NO: 1, but is not limited thereto.

Further, the INO2 gene may include not only the nucleotide sequence of SEQ ID NO: 1 but also a nucleotide sequence having 80% or more, specifically 90% or more, more specifically 95% or more, and much more specifically 99% or more homology with the above sequence and encoding a transcription factor which shows effects substantially identical or corresponding to those of the transcription factor, without limitation. Further, it is apparent that any nucleotide sequence having a deletion, modification, substitution, or addition of some sequence may be within the scope of the present invention, as long as the nucleotide sequence has the above homology.

Information of INO4 and a gene encoding INO4 may be obtained from database such as GenBank at US NIH, and for example, the INO4 gene may have a nucleotide sequence of SEQ ID NO: 2, but is not limited thereto.

Further, the INO4 gene may include not only the nucleotide sequence of SEQ ID NO: 2 but also a nucleotide sequence having 80% or more, specifically 90% or more, more specifically 95% or more, and much more specifically 99% or more homology with the above sequence and encoding a transcription factor which shows effects substantially identical or corresponding to those of the transcription factor, without limitation. Further, it is apparent that any nucleotide sequence having a deletion, modification, substitution, or addition of some sequence may be within the scope of the present invention, as long as the nucleotide sequence has the above homology.

As used herein, the term "OPI1 (OverProducer of Inositol 1)" is a transcription repressor of the transcriptional complex INO2-INO4 in response to phospholipid precursor availability. When precursors become limiting, OPI1 is retained at the endoplasmic reticulum (ER) and INO2-INO4 complex activates INO1 and other genes required for phospholipid biosynthesis, whereas abundant precursor availability results in targeting of OPI1 to the nucleus to repress transcription of these genes. OPI1 binds directly to phosphatidic acid, which is required for ER targeting and may act as a sensing mechanism for precursor availability, as phosphatidic acid becomes rapidly depleted upon phospholipid biosynthesis.

Information of OPI1 and a gene encoding OPI1 may be obtained from database such as GenBank at US NIH, and for example, the OPI1 gene may have a nucleotide sequence of SEQ ID NO: 3, but is not limited thereto.

Further, the OPI1 gene may include not only the nucleotide sequence of SEQ ID NO: 3 but also a nucleotide sequence having 80% or more, specifically 90% or more, more specifically 95% or more, and much more specifically 99% or more homology with the above sequence and encoding a transcription factor which shows effects substantially identical or corresponding to those of the transcription factor, without limitation. Further, it is apparent that any nucleotide sequence having a deletion, modification, substitution, or addition of some sequence may be within the scope of the present invention, as long as the nucleotide sequence has the above homology.

As used herein, the term "homology" refers to identity to a given amino acid sequence or nucleotide sequence and may be expressed as percentage. In the specification, a homologous sequence having activity equal or similar to a given amino acid sequence or nucleotide sequence is expressed as "% homology". For example, homology may be identified using a standard software program which calculates parameters of score, identity and similarity, specifically, BLAST 2.0, or by comparing sequences in a Southern hybridization experiment under stringent conditions as defined. Defining appropriate hybridization conditions are within the skill of the art and may be determined by a method known to those skilled in the art (e.g., J. Sambrook et al., Molecular Cloning, A Laboratory Manual, 2nd Edition, Cold Spring Harbor Laboratory press, Cold Spring Harbor, N.Y., 1989; F. M. Ausubel et al., Current Protocols in Molecular Biology, John Wiley & Sons, Inc., New York).

As used herein, the term "intrinsic expression level" refers to an expression level of mRNA or a protein which is expressed in a parent strain at a natural state or before modification of the expression level of the corresponding gene. This is intrinsically the production degree of a given mRNA or protein in a cell such as a microorganism or a tissue under normal situation or prior to regulating expression of a particular gene. The intrinsic expression level may be compared between kinds of strains, types of cells, and tissues, or compared with an expression level induced by some stimulation. Specifically, the intrinsic expression level may be an mRNA expression level or a protein expression level in a microorganism in which expression of the transcription factor of the phospholipid biosynthetic gene is not regulated.

Another aspect of the present invention provides a recombinant yeast having an increased expression level of INO2 or INO4 or increased expression levels of both of them, as compared with their intrinsic expression levels, or having a decreased expression level of OPI1, as compared with its intrinsic expression level.

As used herein, the term "increased expression level, as compared with the intrinsic expression level" means that a gene encoding a corresponding polypeptide is expressed at a higher level than that under a natural state or before modification, and as a result, a large number of the functional corresponding polypeptide are produced.

In the present invention, specifically, the increased expression levels of INO2 and INO4 may be achieved by, but are not limited to:

1) increasing the copy numbers of the polynucleotides encoding the transcription factors, 2) modifying expression regulatory sequences to increase the expressions of the polynucleotides, 3) modifying the polynucleotide sequences on the chromosome to enhance activities of the transcription factors, or 4) a combination thereof.

1) The increasing of the copy numbers of the polynucleotides may be achieved, but is not limited to, in a form of being operably linked to a vector or in a form of being integrated into the chromosome of a host cell. Specifically, the copy number of the polynucleotide in the chromosome of the host cell may be achieved by introducing into the host cell the vector which is operably linked to the polynucleotide encoding the enzyme of the present invention and replicates and functions independently of the host cell or by introducing into the host cell the vector which is operably linked to the polynucleotide and is able to integrate the polynucleotide into the chromosome of the host cell.

As used herein, the term "vector" refers to a DNA construct including a nucleotide sequence encoding the desired protein, which is operably linked to an appropriate expression regulatory sequence to express the desired protein in a suitable host cell. The regulatory sequence may include a promoter that may initiate transcription, any operator sequence for regulating the transcription, a sequence encoding a suitable mRNA ribosome binding site, and a sequence regulating the termination of transcription and translation. After the vector is introduced into the suitable host cell, it may replicate or function independently of the host genome, and may be integrated into the genome itself.

The vector used in the present invention is not particularly limited, as long as it is able to replicate in the host cell, and any vector known in the art may be used. Examples of commonly used vectors may include a natural or recombinant plasmid which may include a replication origin, a promoter, and a terminator. The replication origin may include an autonomous replication sequence (ARS) of yeast. The autonomous replication sequence of yeast may be stabilized by a centromeric sequence (CEN). The promoter may be selected from the group consisting of a CYC promoter, a TEF promoter, a GPD promoter, a PGK promoter, and an ADH promoter. The terminator may be selected from the group consisting of PGK1, CYC1, and GAL1. The vector may further include a selection marker.

As such, the polynucleotide encoding the desired protein in the chromosome may be replaced by a mutated polynucleotide by using a vector for intracellular chromosomal insertion. The insertion of the polynucleotide into the chromosome may be performed by any method known in the art, for example, homologous recombination, but is not limited thereto.

As used herein, the term "transformation" means the introduction of a vector including a polynucleotide encoding a target protein into a host cell in such a way that the protein encoded by the polynucleotide is expressed in the host cell. As long as the transformed polynucleotide may be expressed in the host cell, it may be integrated into and placed in the chromosome of the host cell, or it may exist extrachromosomally. Further, the polynucleotide includes DNA and RNA encoding the target protein. The polynucleotide may be introduced in any form, as long as it may be introduced into the host cell and expressed therein. For example, the polynucleotide may be introduced into the host cell in the form of an expression cassette, which is a gene construct including all elements required for its autonomous expression. Commonly, the expression cassette includes a promoter operably linked to the polynucleotide, transcriptional termination signals, ribosome binding sites, and translation termination signals. The expression cassette may be in the form of a self-replicable expression vector. Also, the polynucleotide as it is may be introduced into the host cell and operably linked to sequences required for expression in the host cell, but is not limited thereto.

As used herein, the term "operably linked" means a functional linkage between a polynucleotide sequence encoding the desired protein of the present invention and a promoter sequence which initiates and mediates transcription of the polynucleotide sequence.

Next, 2) the modifying of the expression regulatory sequences to increase the expressions of the polynucleotides may be achieved, but is not particularly limited to, by inducing a modification on the sequence by deletion, insertion, non-conservative or conservative substitution of nucleotide sequence, or a combination thereof in order to further enhance the activity of expression regulatory sequence, or by replacing the expression regulatory sequence with a nucleotide sequence having stronger activity. The expression regulatory sequence may include, but is not particularly limited to, a promoter, an operator sequence, a sequence coding for a ribosome-binding site, and a sequence regulating the termination of transcription and translation.

A strong heterologous promoter instead of the original promoter may be linked upstream of the polynucleotide expression unit, and examples of the strong promoter may include a GPD promoter, a TEF promoter, an ADR promoter, CCW12, a GAL promoter. More specifically, a *Saccharomyces cerevisiae*-derived promoter, PGK1 is operably linked to the polynucleotide encoding the enzyme so that its expression rate may be increased, but is not limited thereto.

Furthermore, 3) the modifying of the polynucleotide sequences on the chromosome may be achieved, but is not particularly limited to, by inducing a modification on the expression regulatory sequence by deletion, insertion, non-conservative or conservative substitution of nucleotide sequence, or a combination thereof to further enhance the activity of the polynucleotide sequence, or by replacing the polynucleotide sequence with a polynucleotide sequence having stronger activity.

In an embodiment of the present invention, a PGK1 promoter substitution vector was prepared in order to replace the promoter of the gene by a PGK1 promoter, which is a strong constitutive promoter, for induction of overexpression of INO2 or INO4, and a substitution cassette prepared by using this vector was transformed into a PPD yeast mutant strain to prepare an INO2 or INO4-overexpressing recombinant yeast (Example 2).

As used herein, the term "decreased expression level, as compared with the intrinsic expression level" means that a gene encoding a corresponding polypeptide is not expressed or is expressed at a lower level than that under a natural state or before modification, or the corresponding polypeptide is not functional even though it is expressed.

The term "decreased expression level, as compared with the intrinsic expression level" also means that the gene encoding the corresponding polypeptide is completely inactivated, or its expression level is weak or remarkably low, as compared with the intrinsic expression level, and therefore, the gene is not substantially expressed. The gene inactivation may be either complete (knock-out) or partial (e.g., the gene is a hypomorphic gene which shows an expression level lower than the intrinsic expression level or a product of a mutant gene showing a partial reduction in activity affected thereby).

Specifically, inactivation of OPI1 in the present invention may be achieved by 1) deletion of part or all of the polynucleotide encoding the protein,
2) modification of the expression regulatory sequence to decrease the expression of the polynucleotide,
3) modification of the polynucleotide sequence on the chromosome to weaken the activity of the protein, or
4) a combination thereof, but is not particularly limited thereto.

1) The method of deleting part or all of the polynucleotide encoding the protein may be performed by replacing the polynucleotide encoding the endogenous target protein in the chromosome by a polynucleotide with a partial deletion of a nucleotide sequence or by a marker gene, through a vector for chromosomal gene insertion. The "part" may differ depending on the kind of the polynucleotide, but is specifically 1 bp to 300 bp, more specifically 1 bp to 100 bp, and much more specifically 1 bp to 50 bp.

Next, 2) the method of modifying the expression regulatory sequence to decrease the expression of the polynucleotide may be achieved, but is not particularly limited to, by inducing mutations in the expression regulatory sequence through deletion, insertion, conservative or non-conservative substitution of nucleotide sequence or a combination thereof to further weaken the activity of the expression regulatory sequence, or by replacing the expression regulatory sequence with a nucleotide sequence having weaker activity. The expression regulatory sequence includes a promoter, an operator sequence, a sequence encoding a ribosomal binding site, and a sequence regulating the termination of transcription and translation, but is not limited thereto.

Furthermore, 3) the method of modifying the polynucleotide sequence on the chromosome may be achieved by inducing mutations in the sequence through deletion, insertion, conservative or non-conservative substitution of nucleotide sequence or a combination thereof to further weaken the activity of the protein, or by replacing the polynucleotide sequence with a polynucleotide sequence which is improved to have weaker activity, but is not limited thereto.

In an embodiment of the present invention, a deletion cassette for removing OPI1 was prepared and transformed into a PPD yeast mutant strain to prepare an OPI1-deleted recombinant yeast (Example 3).

According to a specific embodiment, the recombinant yeast was used to compare the production of squalene, 2,3-oxidosqualene, and protopanaxadiol, which are intermediate products in ginsenoside biosynthesis, with that of a control group. As a result, the production was increased in both the INO2- and INO4-overexpressed recombinant yeasts and the OPI1-deleted recombinant yeast, as compared with the control group, and in particular, the greatest production was observed in the INO2-overexpressed recombinant yeast (Example 4, Table 5, Table 6, and FIG. 4).

The recombinant yeast of the present invention may increase production of ginsenoside, squalene and 2,3-oxidosqualene.

As used herein, the term "ginsenoside-producing recombinant yeast" refers to a yeast that naturally has the ability to produce ginsenoside or a yeast prepared by providing a parent strain having no ability to produce ginsenoside with the ability to produce ginsenoside.

As used herein, the term "ginsenoside" refers to a dammarane-type saponin derived from ginseng, or a derivative thereof, and has a unique chemical structure that is different from saponin found in other plants. Examples of the ginsenoside may include, but are not particularly limited to, PPD (protopanaxadiol)-type ginsenoside, PPT (protopanaxatriol)-type ginsenoside, etc. For another example, PPD, PPT, Ra3, Rb1, Rb2, Rb3, Rc, Rd, Re, Rg1, Rg2, Rg3, Rh1, Rh2, Rs1, C-O, C-Y, C-Mc1, C-Mc, F1, F2, compound K, gypenoside XVII, gypenoside LXXV, Rs2, PPD, Re, Rg1, Rf, F1, Rg2, PPT and Rh1 may be used alone or in combination. For still another example, PPD, PPT, compound. K, Rb1, Rb2, Rb3, Rc, Rd, Re, F1, F2, Rg1, Rg2, Rg3, Rh1, Rh2 may be used alone or in combination. Specifically, the ginsenoside may be protopanaxadiol-type ginsenoside.

As used herein, the term "ginsenoside precursor-producing recombinant yeast" refers to a yeast that naturally has the ability to produce a ginsenoside precursor or a yeast prepared by providing a parent strain having no ability to produce a ginsenoside precursor with the ability to produce a ginsenoside precursor.

As used herein, the term "ginsenoside precursor" refers to an intermediate product in the ginsenoside biosynthesis. In the ginsenoside biosynthesis, isopentenyl diphosphate and dimethylallyl diphosphate are produced by a mevalonic acid metabolic pathway, and converted to squalene and 2,3-oxidosqualene which is an oxidized form of squalene. Dammarenediol-II is produced by cyclization of 2,3-oxidosqualene, and various ginsenosides are synthesized from dammarenediol-II. The ginsenoside precursor may include all these intermediate products. The ginsenoside precursor may also include other types of saponin produced through these precursors. The ginsenoside precursor may also include β-amyrin or oleanate.

Specifically, the ginsenoside precursor-producing recombinant yeast may produce squalene or 2,3-oxidosqualene.

In a specific embodiment of the present invention, provided is the recombinant yeast, in which the ginsenoside precursor includes squalene and 2,3-oxidosqualene.

As used herein, the term "squalene" refers to a compound belonging to an isoprenoid-type or a terpenoid-type, and is a polyunsaturated lipid having 6 double bonds and has a chemical formula of $C_{30}H_{50}$. Squalene is an intermediate product in the ginsenoside biosynthesis, and produced via a mevalonic acid pathway. Further, squalene has a strong antioxidant action in the body, and used in biosynthesis of steroid hormones, vitamin D, bile acid, and cholesterol which is a component of cell membrane, and also used as an adjuvant for swine flu vaccine, etc.

As used herein, the term "2,3-oxidosqualene" is an intermediate in the synthesis of lanosterol and cycloartenol which are the cell membrane sterol precursors, as well as saponins including ginsenosides. 2,3-oxidosqualene is produced by oxidation of squalene by squalene epoxidase.

The yeast may be a strain belonging to *Saccharomyces, Zygosaccharomyces, Pichia, Kluyveromyces, Candida, Schizosaccharomyces, Issatchenkia, Yarrowia,* or *Hansenula.*

The strain belonging to *Saccharomyces* may be, for example, *Saccharomyces cerevisiae* (*S. cerevisiae*), *Saccharomyces bayanus* (*S. bayanus*), *Saccharomyces boulardii* (*S. boulardii*), *Saccharomyces bulderi* (*S. bulderi*), *Saccharomyces cariocanus* (*S. cariocanus*), *Saccharomyces cariocus* (*S. cariocus*), *Saccharomyces chevalieri* (*S. chevalieri*), *Saccharomyces dairenensis* (*S. dairenensis*), *Saccharomyces ellipsoideus* (*S. eliipsoideus*), *Saccharomyces eubayanus* (*S. eubayanus*), *Saccharomyces exiguus* (*S. exiguus*), *Saccharomyces florentinus* (*S. florentinus*), *Saccharomyces kluyveri* (*S. kluyveri*), *Saccharomyces martiniae* (*S. martiniae*), *Saccharomyces monacensis* (*S. monacensis*), *Saccharomyces norbensis* (*S. norbensis*), *Saccharomyces paradoxus* (*S. paradoxus*), *Saccharomyces pastorianus* (*S. pastorianus*), *Saccharomyces spencerorum* (*S. spencerorum*), *Saccharomyces turicensis* (*S. turicensis*), *Saccharomyces unisporus* (*S. unisporus*), *Saccharomyces uvarum* (*S. uvarum*), or *Saccharomyces zonatus* (*S. zonatus*).

In a specific embodiment of the present invention, the yeast may be *Saccharomyces cerevisiae* (*S. cerevisiae*), but is not limited thereto.

In general, the *Saccharomyces cerevisiae* is known as one of yeasts used in various fermentation processes, and known to have ability to convert sugars into ethanol.

The ginsenoside-producing yeast may be, but is not particularly limited to, a yeast which is modified to have increased activity of HMG-CoA reductase (tHMG1) which converts HMG-CoA to mevalonic acid and increased activity Panax ginseng-derived squalene epoxidase (PgSE) which converts squalene to 2,3-oxidosqualene, as compared with their intrinsic activities, in order to enhance the mevalonic acid metabolic pathway for increasing the biosynthesis of squalene which is a precursor essential for ginsenoside biosynthesis, and modified to have activity of Panax ginseng-derived dammarenediol-II synthase (PgDDS) which converts 2,3-oxidosqualene to dammarenediol-II, and activities of Panax ginseng-derived cytochrome P450 CYP716A47 (PgPPDS) and Panax ginseng-derived NADPH-cytochrome P450 reductase (PgCPR) which convert dammarenediol-II to protopanaxadiol in order to introduce the ginsenoside biosynthetic pathway.

Still another aspect of the present invention provides the recombinant yeast, in which expression of a gene involved in ginsenoside synthesis is increased, as compared with the intrinsic expression level.

Still another aspect of the present invention provides the recombinant yeast, in which the gene is one or more selected from the group consisting of PgDDS (Panax ginseng, dammarenediol-II synthase), PgPPDS (Panax ginseng cytochrome P450 CYP716A47), PgCPR (P NADPH-cytochrome P450 reductase), tHMG1 (*S. cerevisiae* HMG-CoA reductase) and PgSE (Panax ginseng, squalene epoxidase).

In an embodiment of the present invention, the enzymes involved in the ginsenoside biosynthetic pathway were introduced by transformation, and the enzymes involved in the mevalonic acid metabolic pathway were transcribed from a GPD1 (TDH3) promoter which is a strong constitutive promoter, and thus their expression levels were increased, as compared with their intrinsic expression levels (Example 1).

In this regard, genes encoding the enzymes may include, but are not particularly limited to, specifically nucleotide sequences having 70% or more, more specifically 80% or more, more specifically 90% or more homology with nucleotide sequences of SEQ ID NOS: 4 to 8, respectively.

Still another aspect of the present invention provides a method of preparing the recombinant yeast having improved ability to produce ginsenoside, the method including the step of changing the expression level of the transcription factor of the phospholipid biosynthetic gene in the ginsenoside-producing yeast strain In a specific embodiment of the present invention, provided is the method of preparing the recombinant yeast, in which the expression level of the phospholipid biosynthetic gene, INO2 or INO4, or the expression levels of both of them is/are increased, as compared with their intrinsic expression levels, or the expression level of OPI1 is decreased, as compared with its intrinsic expression level.

The ginsenoside-producing yeast strain, the transcription factor of the phospholipid biosynthetic gene, INO2, INO4, OPI1 and the intrinsic expression level are the same as described above.

In another specific embodiment of the present invention, the ginsenoside-producing yeast strain may have increased expression levels of one or more genes selected from the group consisting of PgDDS (Panax ginseng, dammarenediol-II synthase), PgPPDS (Panax ginseng cytochrome P45G CYP716A47), PgCFR (P NADPH-cytochrome P450 reductase), tHMG1 (*S. cerevisiae* HMG-CoA reductase) and PgSE (Panax ginseng, squalene epoxidase), as compared with their intrinsic expression levels.

Still another aspect of the present invention provides a method of preparing the recombinant yeast having improved ability to produce the ginsenoside precursor, the method including the step of changing the expression level of the transcription factor of the phospholipid biosynthetic gene in the ginsenoside precursor-producing yeast strain In a specific embodiment of the present invention, provided is the method of preparing the recombinant yeast, in which the ginsenoside precursor includes squalene and 2,3-oxidosqualene.

In another specific embodiment of the present invention, provided is the method of preparing the recombinant yeast, in which the expression level of the phospholipid biosynthetic gene, INO2 or INO4, or the expression levels of both of them is/are increased, as compared with their intrinsic expression levels, or the expression level of OPI1 is decreased, as compared with its intrinsic expression level.

The transcription factor of the phospholipid biosynthetic gene, INO2, INO4, OPI1, and intrinsic expression level are the same as described above.

Still another aspect of the present invention provides a method of producing ginsenoside or a precursor thereof, the method including the step of culturing the recombinant yeast.

In the method, the step of culturing the yeast may be performed by, but is not particularly limited to, a known batch, continuous, or fed-batch culturing method. With regard to culture conditions, basic compounds (e.g., sodium hydroxide, potassium hydroxide, or ammonia) or acidic compounds (e.g. phosphoric acid or sulfuric acid) may be used to adjust pH at an appropriate level (e.g., pH 5 to pH 9, specifically pH 6 to pH 8, most specifically pH 6.8), and aerobic conditions may be maintained by introducing oxygen or oxygen-containing gas mixtures into the culture, but are not limited thereto. The culture temperature may be maintained at 20° C. to 45° C., specifically at 25° C. to 40° C. Culturing may be performed for about 10 hours to 160 hours. The ginsenoside produced by the above culture may be secreted into the medium or may remain in the cells.

Furthermore, sugar sources that may be used in the culture medium may include sugars and carbohydrates (e.g., glucose, sucrose, lactose, fructose, maltose, molasses, starch, and cellulose), oils and fats (e.g., soybean oil, sunflower oil, peanut oil, and coconut oil), fatty acids (e.g., palmitic acid, stearic acid, and linoleic acid), alcohols (e.g., glycerol and ethanol), and organic acids (e.g., acetic acid). These substances may be used individually or in a mixture, but are not limited thereto. Nitrogen sources may include nitrogen-containing organic compounds (e.g., peptone, yeast extract, meat extract, malt extract, corn steep liquor, soybean meal, and urea) or inorganic compounds (e.g., ammonium sulfate, ammonium chloride, ammonium phosphate, ammonium carbonate, and ammonium nitrate). These nitrogen sources may also be used individually or in a mixture, but are not limited thereto. Phosphorus sources which may be used include potassium dihydrogen phosphate, dipotassium hydrogen phosphate, or the corresponding sodium salts. These nitrogen sources may also be used individually or in a mixture, but are not limited thereto. The culture medium may include essential growth stimulators, such as metal salts (e.g., magnesium sulfate or iron sulfate), amino acids, and vitamins.

The method may further include the step of recovering the produced ginsenoside. This recovering process may be a step of recovering cultured cells or a supernatant thereof, and a process suitable for the recovery may be selected by those skilled in the art.

The method of recovering the ginsenoside produced in the culturing step of the present invention may be performed by an appropriate method known in the art, for example, in a batch, continuous, or fed-batch manner, to collect the desired product from the culture.

Hereinafter, the present invention will be described in more detail with reference to Examples and Experimental Examples. However, these Examples and Experimental Examples are for illustrative purposes only, and the scope of the present invention is not intended to be limited by these Examples and Experimental Examples.

Example 1: Preparation of PPD Mutant Yeast Strain

To prepare a yeast cell of the present invention, *Saccharomyces cerevisiae* (*S. cerevisiae*) CEN.PK2-1D wild-type strain [(MATα ura 3-52; trp1-289; leu2-3, 112; his3Δ1; MAL2-8; SUC2), EUROSCARF accession number: 30000B] was introduced with a ginsenoside biosynthetic pathway and enhanced a mevalonic acid metabolic pathway to enhance biosynthesis of squalene which is an essential precursor in ginsenoside biosynthesis to prepare protopanaxadiol (PPD) producing yeast strain. This yeast strain was designated as a PPD mutant yeast strain.

Genotype of the PPD strain was *S. cerevisiae* CEN.PK2-1D Δtrp1::$P_{GPD1}$ tHMG1+$P_{GPD1}$ PgSE Δleu2::$P_{GPD1}$ PgDDS+$P_{GPD1}$ PgPPDS+$P_{GPD1}$ PgCPR. Respective genes encoding PgDDS (Panax ginseng, dammarenediol-II synthase, SEQ ID NO: 4), PgPPDS (Panax ginseng cytochrome P450 CYP716A47, SEQ ID NO: 5) and PgCPR (Panax ginseng NADPH-cytochrome P450 reductase, SEQ ID NO: 6) which are ginsenoside biosynthetic enzymes and tHMG1 (*S. cerevisiae* HMG-CoA reductase, SEQ ID NO: 7) and PgSE (Panax ginseng, squalene epoxidase, SEQ ID NO: 8) which are enzymes in a metabolic pathway for enhancing the mevalonic acid metabolic pathway were transcribed and expressed from GPD1 (TDH3) promoter which is a strong constitutive promoter.

Example 2: Preparation of INO2 or INO4-Overexpressing Mutant Yeast Strain

In order to examine whether overexpression of INO2 or INO4, which is involved in phospholipid biosynthesis to increase the size of endoplasmic reticulum, to control cell membrane components, and to induce a stress response against unfolded proteins, in the PPD mutant yeast strain, is involved in growth and PFD producing ability of the mutant yeast strain, mutant yeast strains overexpressing the genes were prepared. First, in order to induce overexpression of INO2 or INO4, a PGK1 promoter substitution vector was prepared for substitution of the promoter of the gene with a strong constitutive PGK1 promoter, and a substitution cassette prepared by using the vector was transformed into the PPD mutant yeast strain to prepare an INO2 or INO4-overexpressing mutant; yeast strain.

In detail, to prepare the PGK1 promoter substitution vector, the strong constitutive PGK1 promoter region sequence from genomic DNA of *S. cerevisiae* CEN.PK2-1D were made to have restriction enzyme recognition sites SacI and XbaI at the 5'- and 3'-ends by PCR (Polymerase Chain Reaction) using a primer combination of PGK1 pro F and PGK1 pro R (Table 1). After amplification, the PCR product was subjected to electrophoresis to obtain a desired fragment. In this regard, PCR was repeated for 25 cycles of denaturation at 95° C. for 30 seconds, annealing at 56° C. for 30 seconds, and elongation at 72° C. for 30 seconds. The amplified fragment was treated with SacI and XbaI, and ligated with a pUC57-URA3HA vector (Ju Young Lee, Chang Duk Kang, Seung Hyun Lee, Young Kyoung Park and Kwang Myung Cho (2015) Engineering cellular redox balance in *Saccharomyces cerevisiae* for improved production of L-lactic acid. Biotechnol. Bioeng., 112, 751-756) treated with the same restriction enzymes, thereby preparing a pUC57-URA3HA-PGK1 vector (FIG. 3).

TABLE 1

Primer sequences and restriction enzymes for preparation of pUC57-URA3HA-PGK1 vector

| Primer | Primer sequence | SEQ ID NO: | Restriction enzyme |
|---|---|---|---|
| PGK pro F | 5'-CGAGCTCAGACGCGAATTTTTCGAAGAAG-3' | 9 | SacI |
| PGK pro R | 5'-GACTAGTTCTAGATGTTTTATATTTGTTGTAAA AAGTAGATAATTACTTCC-3' | 10 | xba I |

PCR was performed by using the prepared pUC57-URA3HA-PGK1 vector as a template and a primer combination of P_INO2 F and P_INO2 R which are homologous recombination sequences of the INO2 promoter region to prepare a cassette for replacing the INO2 promoter by the PGK1 promoter. In the same manner, PCR was performed by using a primer combination of P_INO4 F and P_INO4 R which are homologous recombination sequences of the INO4 promoter region to prepare a cassette for replacing the INO4 promoter by the PGK1 promoter. In this regard, PCR was repeated for 25 cycles of denaturation at 95° C. for 30 seconds, annealing at 56° C. for 30 seconds, and elongation at 72° C. for 2 minutes.

The prepared cassette for INO2 promoter or INO4 promoter substitution was introduced into the PPD mutant yeast strain, respectively. The introduction was performed by a general heat shock transformation method, and after transformation, the cells were cultured in a uracil dropout medium (6.7 g of Yeast Nitrogen Base without amino acids, 0.77 g of CSM minus uracil, 20 g of Glucose per 1 L) to substitute the INO2 promoter or INO4 promoter on the genome with PGK1 promoter by the cassette.

To confirm substitution of the PGK1 promoter in the obtained mutant yeast strain, PCR was performed by using the genome of the cells as a template and a primer combination of INO2 to PGK1 F and INO2 to PGK1 R. As a result, substitution of the PGK1 promoter for the INO2 promoter was confirmed. Further, PCR was performed by using a primer combination of INO4 to PGK1 F and INO4 to PGK1 R. As a result, substitution of the PGK1 promoter for the INO4 promoter was confirmed. Finally, PPD-INO2 ($P_{INO2}$::$P_{PGK1}$) and PPD-INO4 (($P_{INO4}$::$P_{PGK1}$) mutant yeast strains were prepared.

TABLE 2

Primer sequences for preparation of PGK1 promoter substitution cassette and substitution confirmation

| Primer | Primer sequence | SEQ ID NO: |
|---|---|---|
| P_INO2 F | 5'-CATTTAGCAGCGCCAGCGCCCTTCTAAGCTCTTCCATACCTATACGCATGA GGTTTCCCGACTGGAAAGC-3' | 11 |
| P_INO2 R | 5'-TTATCCAGATCTAGGATACCCAGTAATTCGTTCCCAGTTGCTTGTTGCATT GTTTTATATTTGTTGTAAAAAGTAGATAA-3' | 12 |
| P_INO4 F | 5'-AAAAATGAATCCGGGATATTCAATTCTAGGAACCTCGAACTATATTGCATA GGTTTCCCGACTGGAAAGC-3' | 13 |
| P_INO4 R | 5'-TCGGACAATCCCGGCTGTATTGTTTGTATCTCCTTAATATCGTTCGTCATT GTTTTATATTTGTTGTAAAAAGTAGATAA-3' | 14 |
| INO2 to PGK1 F | 5'-GCGCCCTTCTAAGCTCTTCC-3' | 15 |
| INO2 to PGK1 R | 5'-ACCCAGTAATTCGTTCCCAGTTG-3' | 16 |
| INO4 to PGK1 F | 5'-CCGGGATATTCAATTCTAGGAACCT-3' | 17 |
| INO4 to PGK1 R | 5'-TTTCTTCACATTAGCCAGTTCACCC-3' | 18 |

Example 3: Preparation of OPI1-Deleted Mutant Yeast Strain

In order to examine whether deletion of OPI1, which is a repressor to repress expression of the genes involved in phospholipid biosynthesis to increase the size of endoplasmic reticulum, to control cell membrane components, and to induce a stress response against unfolded proteins, in the PPD mutant yeast strain, is involved in growth and PPD producing ability of the mutant yeast strain, a mutant yeast strain where the gene was deleted was prepared. First, a deletion cassette for OPI1 deletion was prepared and transformed into the PDD mutant yeast strain to prepare an OPI1-deleted mutant yeast strain.

In detail, to prepare the cassette for OPI1 deletion, PCR was performed by using the pUC57-URA3HA vector as a template and a primer combination (Table 3) of Del OPI1 F and Del OPI1 R which are OPI1 homologous recombination sequences, thereby preparing the cassette for OPI1 deletion. In this regard, PCR was repeated for 25 cycles of denaturation at 95° C. for 30 seconds, annealing at 56° C. for 30 seconds, and elongation at 72° C. for 1 minute.

TABLE 3

Primer sequences for preparation of OPI1 deletion cassette

| Primer | Primer sequence | SEQ ID NO: |
|---|---|---|
| Del OPI1 F | 5'-TTAAAGCGTGTGTATCAGGACAGTGTTTTTAACGAAGATACTAGTCATTGCCAGTCACGACGTTGTAAAA-3' | 19 |
| Del OPI1 R | 5'-TATAATATTATTACTGGTGGTAATGCATGAAAGACCTCAATCTGTCTCGGAGGTTTCCCGACTGGAAAGC-3' | 20 |

The prepared cassette for OPI1 deletion was introduced into the PPD mutant yeast strain. The introduction was performed by a general heat shock transformation method, and after transformation, the cells were cultured in a uracil dropout medium (6.7 g of Yeast Nitrogen Base without amino acids, 0.77 g of CSM minus uracil, 20 g of Glucose per 1 L) to substitute OPI1 ORF on the genome by the cassette. To confirm deletion of OPI1 in the obtained strain, PCR was performed by using the genome of the cells as a template and a primer combination of OPI1 F and OPI1 R (Table 4). Finally, PPDΔOPI1 (Δopi1) mutant yeast strain was prepared.

TABLE 4

Primer sequences for OPI1 deletion

| Primer | Primer sequence | SEQ ID NO: |
|---|---|---|
| OPI1 F | 5'-GCGTGTGTATCAGGACAGTGT-3' | 21 |
| OPI1 R | 5'-CTGGTGGTAATGCATGAAAGACCTC-3' | 22 |

Example 4: Examination of Growth and PPD Production of Transformed Mutant Yeast Strain Each of the transformed mutant yeast strains was inoculated in 50 ml of a minimal URA drop-out medium containing 2% glucose so that $OD_{600}$ value was 0.5, and each of them was cultured under shaking at 30 rpm to 250 rpm for 144 hours under aerobic conditions. Cell growth during culture was examined by measuring $OD_{600}$ values with a spectrophotometer. Intracellular metabolites (squalene, 2,3-oxidosqualene, Protopanaxadiol) were analyzed by HPLC (High performance liquid chromatography).

As a result of culturing (144 h), cell growth, i.e., $OD_{600}$ values of the culture, and concentrations of the intracellular metabolites are as shown in the following Tables 5 and 6, and FIG. 4.

TABLE 5

Metabolite concentration according to culturing of transformed mutant yeast strain

| Strain | Cell growth ($OD_{600}$) | Squalene (mg/L) | 2,3-Oxidosqualene (mg/L) | Protopanaxadiol (mg/L) |
|---|---|---|---|---|
| Control group | 13.59 | 2.03 | 0.56 | 5.35 |
| INO2-overexpressing strain | 16.47 | 494.50 | 20.23 | 42.32 |
| INO4-overexpressing strain | 14.60 | 1.72 | 0.65 | 11.94 |
| OPI1-deleted strain | 13.35 | 3.44 | 0.33 | 2.21 |

TABLE 6

Fold change of metabolite concentration according to culturing of transformed mutant yeast strain

| Strain | Squalene (mg/L) | 2,3-Oxidosqualene (mg/L) | Protopanaxadiol (mg/L) |
|---|---|---|---|
| Control group | 1 | 1 | 1 |
| INO2-overexpressing strain | 243.01 | 35.81 | 7.90 |
| INO4-overexpressing strain | 0.85 | 1.15 | 2.23 |
| OPI1-deleted strain | 1.69 | 0.58 | 0.41 |

In Tables 5 and 6, the control group represents the PPD mutant yeast strain (*S. cerevisiae* CEN.PK2-1D Δtrp1:: $P_{GPD1}$ tHMG1+$P_{GPD1}$ PGSE Δleu2::$P_{GPD1}$ PgDDS+$P_{GPD1}$ PgPPDS+$P_{GPD1}$ PgCPR), the INO2-overexpressing mutant yeast strain represents PPD-INO2($P_{INO2}$::$P_{PKG1}$), the INO4-overexpressing mutant yeast strain represents PPD-INO4 ($P_{INO4}$::$P_{PKG1}$), and the OPI1-deleted mutant yeast strain represents PPDΔOPI1 (Δopi1). The values in Table 6 represent fold change of each metabolite produced in each prepared mutant yeast strain when a production concentration of each metabolite (squalene, 2,3-oxidosqualene, protopnanxadiol) produced in control yeast strain was taken as 1.

The above results showed that transformation of the mutant yeast strains did not greatly influence the cell growth. Further, the results of measuring the concentrations of the intracellular metabolites showed that increased phospholipid biosynthesis by INO2 and INO4 overexpression or OPI1 deletion led to increased size of endoplasmic reticulum to increase metabolites of ginsenoside biosynthesis, finally indicating improvement of ginsenoside producing ability.

Effect of the Invention

A recombinant yeast having improved ability to produce ginsenoside of the present invention is modified to have an increased expression level of INO2 having a nucleotide sequence of SEQ ID NO: 1 or INO4 having a nucleotide sequence of SEQ ID NO: 2 or increased expression levels of both of them, as compared with their intrinsic expression levels, or to have a decreased expression level of OPI1 having a nucleotide sequence of SEQ ID NO: 3, as compared with its intrinsic expression level, and as a result, it has improved ability to produce ginsenoside. Accordingly, the recombinant yeast may be effectively used in the production of ginsenosides.

What is claimed is:

1. A method of preparing ginsenoside or a precursor thereof, the method comprising the step of culturing a recombinant yeast for producing ginsenoside or a precursor thereof, wherein an expression level of a INO2 (INOsitol requiring 2) gene is increased, as compared with its intrinsic expression level, wherein the INO2 (INOsitol requiring 2) gene comprises the nucleotide sequence of SEQ ID NO: 1, and
wherein the precursor is squalene, 2,3-oxidosqualene or protopanaxadiol.

2. The method of claim 1, wherein the yeast is selected from the group consisting of *Saccharomyces cerevisiae* (*S. cerevisiae*), *Saccharomyces bayanus* (*S. bayanus*), *Saccharomyces boulardii* (*S. boulardii*), *Saccharomyces bulderi* (*S. bulderi*), *Saccharomyces cariocanus* (*S. cariocanus*), *Saccharomyces cariocus* (*S. cariocus*), *Saccharomyces chevalieri* (*S. chevalieri*), *Saccharomyces dairenensis* (*S. dairenensis*), *Saccharomyces ellipsoideus* (*S. ellipsoideus*), *Saccharomyces eubayanus* (*S. eubayanus*), *Saccharomyces exiguus* (*S. exiguus*), *Saccharomyces florentinus* (*S. florentinus*), *Saccharomyces kluyveri* (*S. kluyveri*), *Saccharomyces martiniae* (*S. martiniae*), *Saccharomyces monacensis* (*S. monacensis*), *Saccharomyces norbensis* (*S. norbensis*), *Saccharomyces paradoxus* (*S. paradoxus*), *Saccharomyces pastorianus* (*S. pastorianus*), *Saccharomyces spencerorum* (*S. spencerorum*), *Saccharomyces turicensis* (*S. turicensis*), *Saccharomyces unisporus* (*S. unisporus*), *Saccharomyces uvarum* (*S. uvarum*), and *Saccharomyces zonatus* (*S. zonatus*).

* * * * *